United States Patent [19]
Ciolli

[11] Patent Number: 4,779,078
[45] Date of Patent: Oct. 18, 1988

[54] COMBUSTIBLE GAS DETECTOR

[76] Inventor: Henry J. Ciolli, 44555 N. Bunkerhill, Mt. Clemens, Mich. 48044

[21] Appl. No.: 14,850

[22] Filed: Feb. 13, 1987

[51] Int. Cl.[4] ............................................. G08B 17/10
[52] U.S. Cl. .................................... 340/634; 73/27 R
[58] Field of Search ............... 340/634, 628, 630, 631, 340/633; 73/23, 27 R; 338/34

[56] References Cited

U.S. PATENT DOCUMENTS 3,276,004  4/1963  Mayo .................................... 340/634
4,150,370  4/1979  Bradshaw ........................... 340/634

OTHER PUBLICATIONS

Figaro, Gas Sensors #711 & #812, Apr. 1975.

Motorola, Solid State Gas/Smoke Detector Systems, by Al Pshaenich © 1974.

Primary Examiner—Joseph A. Orsino
Assistant Examiner—Jeffery A. Hofsass
Attorney, Agent, or Firm—James R. Ignatowski; Remy J. VanOphem

[57] ABSTRACT

A combustible gas detector having a transformer, a gas detector, a buzzer, a capacitor connected in parallel with the buzzer, an electronic switch, and two resistors. The gas detector has a resistive element which varies in the presence of a combustible gas. The resistive element and one of the resistors form a voltage divider which produces a potential triggering the electronic switch to energize the buzzer upon the detection of a combustible gas. The capacitor modifies the wave form across the buzzer causing it to produce a unique cricket-like sound.

16 Claims, 1 Drawing Sheet

COMBUSTIBLE GAS DETECTOR

BACKGROUND OF THE INVENTION

1. Field of the Invention

The invention is related to the field of combustible gas detectors and, in particular, to a very simple combustible gas detection circuit which produces a uniquely identifiable cricket-like sound upon the detection of a combustible gas.

2. Description of the Prior Art

Combustible gas sensors are commercially available and a wide variety of circuits using these sensors are known in the art. Probably the best known and most widely used combustible gas sensors are the semi-conductor gas sensors manufactured by Figaro Engineering Inc. of Osaka, Japan. A detailed description of these solid state combustible gas sensors and a variety of circuits using the sensors are contained in a paper entitled "Semi-Conductor Gas Sensor" and a brochure entitled "Figaro Gas Sensor TGS 813" available from Figaro Engineering's United States affiliate Figaro U.S.A. Inc., of Wilmette, Ill.

In addition to the circuits shown in the Figaro paper and brochure cited above, Kasahara, in U.S. Pat. No. 3,686,655, discloses two different alarm circuits. In the first circuit, the gas sensor is connected in series with a neon lamp which acts as an oscillator energizing a speaker which is connected in parallel with the neon lamp. In the second circuit, the speaker is connected in series with a Darlington-type amplifier. The gas sensor is part of a voltage divider, the center tap of which is connected to a neon lamp which acts as an oscillator applying an AC current to the base of the Darlington amlifier. Benedict, in U.S. Pat. No. 3,733,595, discloses several circuits in which a gas sensor is part of a voltage divider supplying an actuating potential to the base of a power transistor. The power transistor actuates a relay switch supplying power to a buzzer or a bell. Caillouet, Jr., U.S. Pat. No. 3,750,123, discloses an alarm circuit in which the gas sensor is part of a voltage divider network which supplies the base potential to a power transistor which actuates a relay supplying electrical power to a buzzer. In a circuit similar to that taught by Caillouet, Jr., Paige et al, in U.S. Pat. No. 4,007,456, discloses an alarm circuit having a comparator between the voltage divider and the base of the power transistor.

Ichinose et al, in U.S. Pat. No. 4,170,770, discloses an alarm circuit in which the gas sensor actuates a Darlington-type amplifier in series with a photocoupler. The photocoupler is part of a resistance divider circuit which supplies the trigger voltage to a triac connected in series with a buzzer. The buzzer is connected between the AC input terminals of the circuit. Hall, Jr., is U.S. Pat. No. 4,443,793, discloses a gas detection circuit in which the gas sensor is one branch of a Wheatstone bridge having its opposite output corners connected to the input of a comparator. The output of the comparator is connected to a power transistor connected in series with an alarm. A diode rectifies the output of the transformer to supply a DC current to the Wheatstone bridge, the comparator, and the power transistor. Finally, Buonavita, U.S. Pat. No. 4,480,252, discloses a gas detection circuit in which the Wheatstone bridge receives a regulated DC voltage at its input terminals. The Wheatstone bridge has a pair of gas sensors and the output of the Wheatstone bridge is connected to a comparator which actuates an alarm in response to the detection of the combustible gas.

The invention is a combustible gas detector having a very simple circuit with a minimum number of components and which produces a uniquely identifiable cricket-like sound.

SUMMARY OF THE INVENTION

The invention is a combustible gas detector for home and work place applications which is capable of detecting the existence of combustible gases, such as methane, propane, alcohol, and butane before they reach explosive levels in the atmosphere. The combustible gas detector includes a housing and a combustible gas detection circuit. The housing has a base to which is attached an electrical plug adapted to be received in a conventional household 110 volt AC electrical outlet and a plastic cover having vents permitting a free flow of air bearing the combustible gases through the interior of the housing.

The combustible gas detection circuit includes a transformer for transforming the 110 volt AC potential received from the household electrical outlet to a 12 volt AC source of electrical power. The secondary winding of the transformer has a center tap providing an intermediate 5.5 volt potential for the operation of the detector portion of the circuit. The detector portion of the circuit includes a combustible gas detector having a resistive element whose resistivity decreases as a function of the quantity of a combustible gas present. The combustible gas sensor also has a heater element which maintains the resistive element at a predetermined temperature for optimum sensitivity. One end of the heater element and the resistive element are connected to the center tap of the secondary winding. The other end of the heater element is connected to one end of the secondary winding while the other end of the resistive element is serially connected to a first resistor to form a voltage divider between the center tap and the one end of the secondary winding. The combustible gas detection circuit also includes a buzzer for producing an audible sound. The buzzer has its electrical input connected to the other end of the secondary winding and its electrical output connected to the anode of a silicon controlled rectifier. The cathode of the silicon controlled rectifier is connected to the one end of the secondary winding. The gate of the silicon controlled rectifier is connected to the junction between the resistive element of the combustible gas sensor and the first resistor through a current limiting resistor. A capacitor is connected in parallel with the buzzer which modifies the current flow through the buzzer causing it to produce a distinctive cricket-like sound.

One object of the disclosed combustible gas detector is to produce a distinctive sound in response to the presence of a combustible gas, which sound is readily distinguishable from all other types of household buzzers, such as used in doorbells, smoke detectors, stove or microwave timers, alarm clocks, washing machines, or any other type of household appliance or warning device. Another object of the invention is to produce a reliable combustible gas detector which has a minimum number of components, is easy to produce, and can be manufactured at a cost within the range of the majority of the potential users. These and other objectives will become more apparent from a reading of the specification in conjuction with the appended drawings.

DETAILED DESCRIPTION OF THE PREFERRED EMBODIMENT

Figure 1:
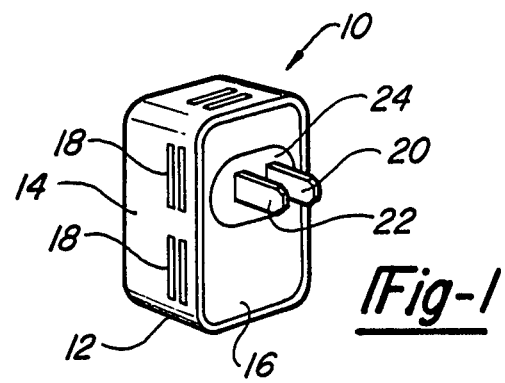
FIG. 1 is a perspective view of the combustible gas detector showing its external configuration.

Referring to FIG. 1, a "Cricket" combustible gas detector 10 with an enclosed housing 12 having a cover 14 and a base 16 is illustrated. The cover 14 is detachable from the base 16 and has a plurality of vents 18 which permit a free flow of gases and combustible vapor into the interior of the housing 12. Protruding from the base 16 are a pair of electrical contact blades 20 and 22 which are part of a conventional electrical plug 24 which is designed to be received in a conventional household 110 volt AC electrical outlet. This permits the "Cricket" combustible gas detector 10 to be wall mounted in any desired location having a conventional 110 volt AC electrical outlet without the need for mounting brackets, hooks, or any other means for attaching the detector to a stove or a wall.

Figure 2:
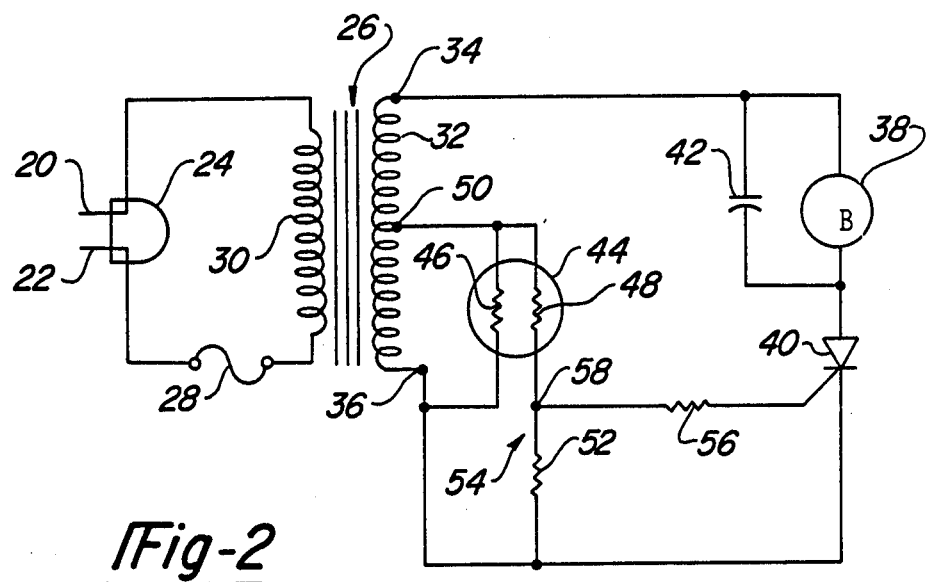
FIG. 2 is a circuit diagram of the combustible gas detection circuit.

The housing 12 encloses a combustible gas detection circuit as shown in FIG. 2. This circuit has a transformer 26 having an internal fuse 28. The transformer 26 has a primary winding 30, the opposite ends of which are connected to the contact blades 20 and 22, respectively, of the electrical plug 24 and a secondary winding 32 for generating a secondary AC voltage in the range form 10 to 14 volts. The secondary winding 32 has a center tap 50 which provides electrical power to the detector portion of the circuit at an intermediate AC potential in the range from 5 to 6 volts. In the preferred embodiment, the secondary AC potential is 12 volts and the intermediate AC potential is 5.5 volts.

Figure 3:
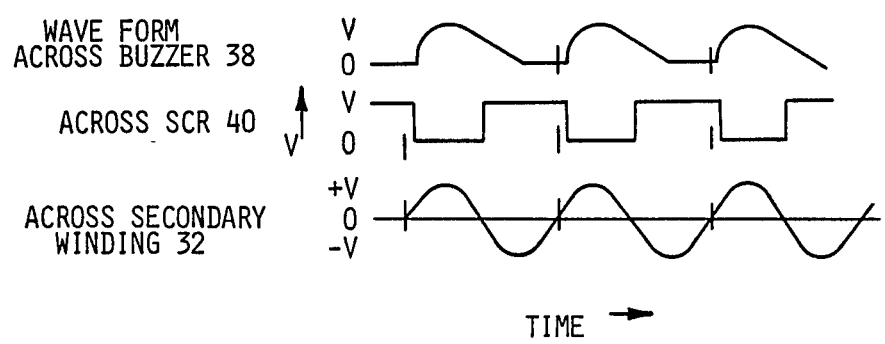
FIG. 3 shows the voltage wave forms across the secondary winding 32, SCR 40, and the buzzer 38 when the combustible gas sensor 44 is detecting a combustible gas.

One end 34 of the secondary winding 32 is connected to an input terminal of a buzzer 38, such as ARK model 35D1 solid state buzzer manufactured by ARK Electronics Limited of Taipei, Taiwan. The output terminal of the buzzer 38 is connected to the anode of a SCR (silicon controlled rectifier) 40, such as silicon controlled rectifier C 106B manufactured by General Electric Company of Schenectady, New York. The cathode of the SCR 40 is connected to the other end 36 of the secondary winding 32. A capacitor 42 is connected in parallel with the buzzer 38 which, when the SCR is in a conductive state, produces the wave form across the buzzer 38, as shown in FIG. 3. This wave form causes the buzzer to produce the uniquely identifiable cricket-like sound which distinguishes the detection of a combustible gas from any other type of alarm buzzer normally used in the household.

A solid state combustible gas sensor 44, such as Figaro gas sensor TGS 813 manufactured by Figaro Engineering Inc. of Osaka, Japan, has a heater element 46 and a resistive element 48 sensitive to the combustible gases. One end of the heater element 46 and one end of the resistive element 48 are connected to the center tap 50 of the secondary winding 32. The other end of the heater element 46 is connected to the other end 36 of the secondary winding 32. The other end of the resistive element 48 is connected in series with a resistor 52 to form a voltage divider network 54 between the center tap 50 and the other end 36 of the secondary winding 32. The combustible gas sensitive resistive element is a sintered tin oxide "N" type semi-conductor material whose resistive value decreases significantly in the presence of a combustible gas or vapor. A current limiting resistor 56 is connected from the junction 58 formed between the resistive element 48 and the resistor 52 to the gate of the silicon controlled rectifier SCR 40.

The operation of the circuit is as follows:

When the plug 24 is inserted into a 110 volt electrical outlet the secondary 10 to 12 volt AC potential is generated across the buzzer 38 and the SCR 40. At the same time the intermediate 5 to 6 volt AC potential is applied across the heater element 46 and the voltage divider network 54. In the absence of a combustible gas, the resistivity of the resistive element 48 is more than ten times greater than the value of the resistor 52 such that the potential at the junction 58 which is applied to the gate of the SCR 40 is approximately 0.12 volts. This potential is below the 0.6 volt crossover potential required to trigger the SCR 40 to the conductive state. Therefore, the buzzer 38 is not energized and the "Cricket" combustible gas detector 10 is silent.

In the presence of a combustible gas, the resistivity of the resistive element 48 decreases significantly such that during the positive half of the intermediate AC potential applied acrosss the voltage divider network 54 the potential at the junction 58 increases above 0.6 volts which, when applied to the gate of the SCR 40 through the resistor 56, renders the SCR 40 fully conductive energizing the buzzer 38. The SCR 40 will remain conductive only during the positive portion of the secondary AC potential generated across the secondary winding 32 keeping the buzzer 38 in a energized state. The negative portion of the secondary AC potential will back bias the SCR 40, rendering it nonconductive. At the same time, the potential at the junction 58 of the voltage divider network 54 will decrease below the cross-over potential of the SCR 40, holding it in a nonconductive state until the next positive portion of the secondary AC potential across the secondary winding 32 occurs. The capacitor 42 will discharge the buzzer 38, keeping it energized for a short period of time after the SCR 40 is rendered nonconductive, as shown by the wave form on FIG. 3. This will enable the buzzer to produce the distinctive chirping cricket-like sound.

When the concentration of the combustible gas diminishes to a safe level, the resistivity of the resistive element 48 increases to a value such that the potential applied to the gate of the SCR 40 during the positive half of the intermediate AC potential is below the 0.6 volt. This will place the SCR 40 in a nonconductive state and deactivate the buzzer 38. Therefore, the combustible gas detector will only emit its audible sound when the concentration of the combustible gas is above a predetermined level, and will return to a silent state when the level of the combustible gas is below this level.

The circuit also has a self-test feature which occurs immediately after the combustible gas detector 10 is first plugged into an AC outlet. When cold, the resistivity of the resisive element 48 of the combustible gas sensor 44 is sufficiently low to cause the potential at the junction 58 to be above the cross-over potential of the SCR 40. Therefore, the SCR 40 will be rendered conductive energizing the buzzer 38. As the heater element 46 heats the resistive element 48, oxygen is dissociatively absorbed on the surface of the resistive element 48. As a result, an electron depletion layer develops which causes potential barriers against bulk conductivity to be formed at the grain boundaries of the resistive element 48. These potential barriers prevent the conduction of electrons across the grain boundaries increasing the resistivity of the resitive element 48. This reaction takes place very rapidly such that the potential at the junction 58 falls below the cross-over potential (0.6 volts) of the SCR 40 within three to five seconds after the combustible gas detector 10 is plugged into the 110 volt AC outlet. During this three to five second period the buzzer 38 will emit its distinctive chirping sound, signifying that the combustible gas detector 10 is operational.

As can be seen, the "Cricket" combustible gas detection circuit has only seven components, the transformer 26, the buzzer 38, the SCR 40, the capacitor 42, the gas sensor 44, the resistor 52, and the current limiting resistor 56. In the preferred embodiment of the circuit shown in FIG. 2, the resistivity of the resistor 52 is 750 ohms, the resistivity of the current limiting resistor 56 is 39,000 ohms, and the capacitance of the capacitor 42 is 15 microfarads.

It is not intended that the combustible gas detector be limited to the exact configuration shown in FIG. 1 or the exact circuit arrangement shown in FIG. 3. It is recognized that those skilled in the art may make changes which are viable alternatives within the invention as described herein and set forth in the appended claims.

What is claimed is as follows:

1. A combustible gas detector comprising:
   an enclosed housing having a cover and a base, said cover having at least one vent for permitting gases to flow therethrough and said base having an electrical plug adapted to be received in a conventional 110 volt AC outlet; and
   a combustible gas detection circuit disposed in said housing, said combustible gas detection circuit comprising:
     a transformer having a primary winding connected to said electrical plug and a secondary winding for generating a secondary AC potential, said secondary winding having a center tap for outputing an intermediate AC potential;
     a buzzer for producing an audible sound, said buzzer having an input terminal connected to one end of said secondary winding and an output terminal;
     a silicon controlled rectifier having an anode connected to said output terminal of said buzzer, a cathode connected to the other end of said secondary winding and a gate;
     a combustible gas sensor having a heater element connected between said center tap and said other end of said secondary winding and a resistive element having a resistivity variable as a function of the presence of a combustible gas, said resistive element having one end attached to said center tap; and
     a first resistor connected between the other end of said resisitive element and said other end of said secondary winding to form a voltage divider, the junction between said resistive element and said first resistor being connected to said gate of said silicon controlled rectifier.

2. The combustible gas detector of claim 1 having a capacitor connected in parallel with said buzzer to cause said buzzer to produce a cricket-like chirping sound.

3. The combustible gas detector of claim 2 having a current limiting resistor connected between said junction formed between said resistive element and said first resistor and said gate of said silicon controlled rectifier.

4. The combustible gas detector of claim 1 wherein said secondary potential is an AC potential in the range from 10 to 14 volts and said intermediate potential is an AC potential in the range from 5 to 6 volts.

5. The combustible gas detector of claim 1 wherein said secondary potential is preferably 12 volts and said intermediate potential is preferably 5.5 volts.

6. A circuit for a combustible gas detector comprising:
   a transformer having a 110 volt AC primary winding and a secondary winding for generating an AC potential in the range from 10 to 14 volts, said secondary winding having a center tap outputing an intermediate AC potential in the range from 5 to 6 volts;
   a buzzer for producing an audible sound, said buzzer having an input terminal connected to one end of said secondary winding and an output terminal;
   a silicon controlled rectifier having an anode connected to said output terminal of said buzzer, a cathode connected to the other end of said secondary winding and a gate;
   a combustible gas sensor having a resistive element which, when heated to a predetermined temperature, has a resistive value which decreases in response to the presence of a combustible gas, and a heater element for heating said resistive element to said predetermined temperature, said heater element being connected between said center tap and said other end of said secondary winding;
   a first resistance serially connected to one end of said resistive element to form a voltage divider, said voltage divider having one end connected to said center tap and the other end connected to said other end of said secondary winding; and
   a second resistance connected between said gate and the junction between said resistive element and said first resistance.

7. The circuit of claim 6 having a capacitor connected in parallel with said buzzer for modifying the wave form across said buzzer to cause it to produce a cricket-like chirping sound.

8. The circuit of claim 7 wherein said capacitor has a capacitance in the range from 10 to 20 microfarads.

9. The circuit of claim 8 wherein the preferred capacitance of said capacitor is 15 microfarads.

10. The circuit of claim 8 wherein said first resistance has a resistance value in the range from 700 to 800 ohms and said second resistance has a resistance value in the range from 30,000 to 50,000 ohms.

11. The circuit of claim 10 wherein said first resistance has a resistance of 750 ohms and said second resistance has a resistance of 39,000 ohms.

12. A combustible gas detector comprising:
   a base;
   an electrical plug attached to said base, said electrical plug attached to be received in a conventional household 110 volt AC outlet;
   a transformer mounted on said base, said transformer having a primary winding and a secondary winding, said primary winding being connected to said electrical plug to receive the 110 volt AC potential from said 110 volt AC outlet, said secondary winding generating a secondary AC potential in the range from 10 to 14 volts and a center tap providing an intermediate potential in the range from 5 to 6 volts;

a buzzer for producing an audible sound, said buzzer having an input terminal connected to the one end of said secondary winding and an output terminal;

a solid state switch connected between said output terminal of said buzzer and the other end of said secondary winding, said solid state switch controlling current flow through said buzzer;

a combustible gas sensor having a resistive element whose resistivity decreases in the presence of a combustible gas;

a first resistor connected in series with said resistive element to form a voltage divider, one end of said voltage divider being attached to said center tap of said secondary winding and the other end of said voltage divider being attached to said other end of said secondary winding, the junction between said resistive element and said first resistor of said voltage divider being connected to said solid state switch and said solid state switch being responsive to the potential at said junction to control the current flow through said buzzer;

a capacitor connected in parallel across said buzzer to continue the current flow through said buzzer for a short period of time after said solid state switch is turned off; and a cover attachable to said base for enclosing said transformer, said combustible gas sensor, said first resistor, said buzzer, said solid state switch, and said capacitor, said cover having at least one vent permitting air and any ambient combustible gases to pass inside said cover and be detected by said combustible gas sensor.

13. The combustible gas detector of claim 12 wherein said combustible gas sensor has a heater element for heating said resistive element to a predetermined operating temperature, one end of said heater element is connected to said center tap and the other end is connected to said other end of said secondary winding.

14. The combustible gas detector of claim 12 wherein said solid state switch is a silicon controlled rectifier having an anode connected to said output terminal of said buzzer, a cathode connected to said other end of said secondary winding and a gate connected to the junction between said resistive element and said first resistor.

15. The combustible gas detector in claim 14 having a second resistance connected between said gate of silicon controlled rectifier and the junction between said resistive elements and said first resistor.

16. The combustible gas detector of claim 15 wherein the resistance of said first resistor is between 700 and 800 ohms, the resistance of said second resistance is between 30,000 and 40,000 ohms and the capacitance of said capacitor is between 10 and 25 microfarads.

* * * * *

UNITED STATES PATENT AND TRADEMARK OFFICE
CERTIFICATE OF CORRECTION

PATENT NO.  : 4,779,078
DATED       : October 18, 1988
INVENTOR(S) : Henry J. Ciolli It is certified that error appears in the above-identified patent and that said Letters Patent is hereby corrected as shown below:

Column 1, line 36, delete "amlifier" and insert ---- amplifier ----.

Column 1, line 55, delete "is" and insert ---- in ----.

Column 4, line 5, delete "resistive" and insert ---- resistance ----.

Column 4, line 63, delete "resisive" and insert ---- resistive ----.

Column 5, line 7, delete "resitive" and insert ---- resistive ----.

Column 5, line 64, delete "resisitive" and insert ---- resistive ----.

Column 6, line 65, delete "attached" and insert ---- adapted ----.

Signed and Sealed this

Thirteenth Day of June, 1989

*Attest:*

DONALD J. QUIGG

*Attesting Officer*   *Commissioner of Patents and Trademarks*